United States Patent [19]

Grimmett et al.

[11] Patent Number: 5,670,170
[45] Date of Patent: Sep. 23, 1997

[54] PHARAMACEUTICAL FORMULATION

[75] Inventors: Francis Walter Grimmett; Nigel Philip Davidson, both of Worthing, England

[73] Assignee: Beecham Group p.l.c., Brentford, United Kingdom

[21] Appl. No.: 444,114

[22] Filed: May 18, 1995

Related U.S. Application Data

[63] Continuation of Ser. No. 937,867, filed as PCT/GB91/00637, Apr. 22, 1991, abandoned.

[30] Foreign Application Priority Data

Apr. 27, 1990 [GB] United Kingdom .................. 9009473

[51] Int. Cl.$^6$ ........................................ A61K 9/14
[52] U.S. Cl. ............................ 424/489; 424/466
[58] Field of Search ........................ 424/466, 489

[56] References Cited

U.S. PATENT DOCUMENTS

| 3,872,227 | 3/1975 | Hoff et al. | 424/271 |
| 4,888,177 | 12/1989 | Gergely et al. | 424/466 |
| 5,225,197 | 7/1993 | Bolt et al. | 424/440 |

FOREIGN PATENT DOCUMENTS

| 0080862 | 11/1982 | European Pat. Off. . |
| 0396335 | 7/1990 | European Pat. Off. . |
| 1300998 | 12/1972 | United Kingdom . |

OTHER PUBLICATIONS

Eugene L. Parrott, "Pharmaceutical Technology". Solid Pharmaceuticals p.64–65.

Primary Examiner—Jyothsna Venkat
Attorney, Agent, or Firm—Dara L. Dinner; Stephen Venetianer; Edward T. Lentz

[57] ABSTRACT

A pharmaceutical formulation comprises a medicament and an effervescent couple, plus optionally other excipients. Preferred medicaments are antibiotics, together with a citric acid—sodium bicarbonate couple. The formulation is provided for make up with water into an antibiotic suspension.

11 Claims, No Drawings

PHARAMACEUTICAL FORMULATION

This is a continuation of application Ser. No. 07/937,867, filed Oct. 16, 1992, now abandoned which is a 371 of PCT/GB/ 91/00637 filed Apr. 22, 1991.

This invention relates to pharmaceutical compositions for oral administration of antibiotics and other medicaments with unpleasant taste characteristics, and particularly to compositions formulated for dispersion in water prior to administration.

From the point of view of bioavailability, the preferred form of administration of sparingly soluble medicaments such as β-lactam antibiotics is often an aqueous suspension. However, there are problems associated with this form of administration. For example, such preparations in multidose form may have a limited shelf life, and usual methods of dose measurement lack accuracy.

Single dose powders for reconstitution in sachet form offer the advantages of suspensions without the problems of instability and measuring inaccuracy. Unfortunately, in the case of β-lactam antibiotics the problem of the unpleasant taste of these medicaments remains with such powder formulations.

Accordingly the present invention provides a pharmaceutical formulation, being a granular product containing a medicament and an effervescent couple which comprises a basic ingredient and an acidic ingredient, the basic ingredient liberating carbon dioxide when it and the acidic ingredient are contacted with water, which disperses in water to produce a suspension which can be swallowed by a patient.

It has been found that the inclusion of an effervescent couple in pharmaceutical granules can enable very rapid formation (eg 10–30 seconds) of a suspension in a small volume of water for a relatively low fill weight presentation, in comparison to traditional sachet presentations of β-lactam antibiotics, without recourse to the use of additional disintegrating agents. The resulting suspension is found to be highly palatable and can consequently easily be swallowed by a patient.

Such sachet presentations are thus well-accepted by patients, especially small children and other groups of patients who may otherwise find the medicine difficult to take and who might otherwise refuse treatment. In addition there are commercial advantages of such a presentation. For example, a low weight product reduces raw material costs, enables more unit doses per batch and simplifies the manufacturing and packaging processes. The granular product of the invention also has good flow characteristics which result in improved sachet filling performance, ensuring that sachets may be well sealed.

Preferred medicaments are β-lactam antibiotics such as penicillins and cephalosporins, especially amoxycillin and ampicillin preferably, amoxycillin trihydrate. A preferred β-lactamase inhibitor is clavulanic acid, preferably as potassium clavulanate. Typically, the ratio of antibiotic to inhibitor is 4:1 or 2:1 by weight, but ratios of 12:1 to 1:1 may be used. The weight of the antibiotic in a unit dose may range from 125 mg to 3 g, expressed in terms of the activity of the antibiotic. The weight of antibiotic in the formulation, calculated as the free acid, may range from 5% to 50% preferably 40% to 50% based on the weight of the formulation.

The effervescent couple typically comprises citric acid or sodium hydrogen citrate and sodium bicarbonate, but other physiologically acceptable and/alkaline or alkaline earth metal carbonate mixtures may be used, for example tartaric, adipic, fumaric or malic acids, and sodium, potassium or calcium bicarbonates or sodium glycine carbonate.

The weight of acidic ingredient may be in the range 0.5% to 20%, eg 1.0% to 10%, preferably 1.5% to 5%, of the weight of the formulation.

The weight of the basic component may be in the range 0.5% to 30%, eg 1.0 to 20%, preferably 1.5% to 10%, of the weight of the mixture.

The granular formulation may contain any of the conventional excipients such as diluents/fillers/bulking agents used in pharmaceutical products, for example lactose, fructose, mannitol or sorbitol alone or in combination eg making up 0.1% to 60%, typically 30% to 50% by weight of the formulation. Other conventional excipients may include lubricants eg making up 0.1% to 3%, typically 0.25% to 2.5% by weight of the formulation such as magnesium stearate, sweetening agents such as sugars sodium saccharin and aspartame eg making up 0.1% to 2% by weight and flavouring agents eg lemon and/or lime typically making up 0 to 20% by weight of the formulation. Multidose products for reconstitution may include suspending agents such as Xanthan gum eg Keltrol-Trade Mark, (a sodium, potassium or calcium salt of a partially acetylated polysaccharide containing D glucose, D mannose and D glucoronic acid units). Alternative thickeners are hydroxypropyl methyl celluloses or hydroxypropyl cellulose (eg Klucel-Trade Mark), sodium carboxymethyl-cellulose-carmellose or aerosil. Typically such suspending agents may be present at 1% to 5% by weight. Multidose products may also include preservatives such as sodium benzoate, typically at 0.2% to 1.5% by weight. A desiccant such as syloid (Trade Mark) may also be included for moisture sensitive antibiotics.

The invention also provides a process for the preparation of such a pharmaceutical formulation, comprising admixing the medicament and the effervescent couple, and subsequently compacting the mixture into a granular product.

A preferred size fraction for the granular formulation of the invention is less than 1000 μ, eg 30 μ to 600 μ, particularly 100 μ to 425 μ. To prepare the granular formulation of the invention the starting components, especially the medicament are preferably finely milled to a particle size of less than 200 μ, to result in a particle size of typically <30 μ–200 μ. Starting materials of <30 μ–1000 μ (with the exception of the medicament) may be used. The coarse excipient fraction may improve flow and hence will aid the compaction process.

Typically the manufacturing process involves the following stages:

(a) Mill the medicament finely at fast speed, through a 0.020 inch (0.5 mm) screen.

(b) Mill the diluent/filler/bulking agent and sweetners at slow speed through an 0.040 (1.0 mm) inch screen.

(c) Sieve through a 20 mesh screen the flavours, effervescent couple components and magnesium stearate.

(d) Blend the components and compress the mix on a tabletting or slugging machine to give compacts (slugs) of medium density or roller compact the mix to a medium pressure and product density.

(e) Pass the compacted material through a mill at low speed fitted with a screen, to form granules.

(f) Sieve the granules and collect the desired size fraction. Recycle the coarser and finer material to the compaction equipment if it is desired to limit the size range of the granule.

(g) Fill or tablet the granule under low humidity cover.

Preferably the entire process (a) to (g) is carried out under a low humidity, eg <30% RH and a low temperature eg 10°–25° C. Preferably the components are used anhydrous or substantially anhydrous.

The granular formulation may be coated with an acid soluble polymer to assist rapid and widespread release of the medicament to occur in the stomach, or they may be coated with an enteric (acid resistant polymer) to assist rapid release in the intestine. Suitable acid soluble polymers include Eudragit E (Trade Mark)—a cationic polymer synthesised from dimethylaminoethyl methacrylate, ethylcellulose or ethylcellulose mixtures with water soluble polymers such as hydroxypropyl cellulose or hydroxypropylmethyl cellulose.

The granules are preferably packed in conventional unit dose sachets, eg composed of a laminate of polymer, paper and foil. A common granular formulation may be used at a range of different fill weights to provide a range of unit doses eg 125 mg, 250 mg, 500 mg, 1 g and 3 g of amoxycillin. Alternatively the granular formulation may be provided in jars etc as a multidose presentation for make up in water.

Alternatively the granular formulation may be tabletted, eg by a process of compaction to provide a tablet formulation. Such tablets may each contain a unit dose (as described above) of the medicament and may be provided for administration by swallowing, dispersal in water then swallowing, or as coated pessary or rectal tablets for human or animal patients. The formulation of the invention therefore has a further advantage in providing a common material for administration in sachets or as tablets.

The invention also provides a process for the use of a pharmaceutical formulation as described above in the manufacture of a medicament for the treatment of bacterial infections.

The invention also provides a method of treatment of bacterial infections in humans and animals which comprises the administration of a therapeutically effective amount of a pharmaceutical formulation as described above.

The invention also provides a pharmaceutical formulation as described above for use in the treatment of bacterial infections.

The invention is illustrated by the following Example.

EXAMPLE 1

250 mg. Dose Fizzy Granule (β-lactam antibiotic)

| Ingredients | mg/sachet | (% w/w) |
| --- | --- | --- |
| Amoxycillin Trihydrate equivalent to Amoxycillin free acid | 250.00 | 41.667 |
| Magnesium stearate | 6.75 | 1.125 |
| Citric acid | 12.50 | 2.083 |
| Sodium bicarbonate | 25.00 | 4.167 |
| Sodium saccharin | 2.50 | 0.417 |
| Lemon dry flavour | 27.50 | 4.583 |
| Lime dry flavour | 1.38 | 0.230 |
| Sorbitol B.P. | 90.00 | 15.000 |
| Mannitol U.S.P. | 184.37 | 30.72 |
| Total | 600 mg | 100.00 |

(all of the above ingredients were used in a substantially anhydrous state).

Manufacturing Procedure for Example 1

The amoxycillin was first milled finely at a high speed through an 0.02 inch (0.5 mm) screen. Then the mannitol and sodium saccharin were milled at a slow speed through an 0.04 inch (1 mm) screen. The flavours, citric acid, sodium bicarbonate and magnesium stearate were then sieved through a 20 mesh sieve. The mixture was compressed on a rotary tabletting machine to give compacts of density 0.39–0.40.

The compacted material was then milled at low speed, 1750 rpm, with knives forward and fitted with an 0.097 inch (0.25 mm) screen. The granules were sieved on a 20 mesh overlying an 80 mesh screen and the 20–80 fraction was collected. This granular product could then be filled into containers or sachets, or tabletted in a conventional manner. The procedure was performed in a humidity of 30% RH or less, at 10°–25° C.

Alternative fruity or citrus flavours could be used in the formulation of example 1. Furthermore the quoted percentages could be varied by ±10% without any significant effect on the properties of the formulation.

The quantities of ingredients quoted in example 1 are for a 250 mg unit dose amoxycillin formulation. By simply increasing or decreasing the quoted quantities in direct proportion formulations for unit doses of other weights of amoxycillin can be made up.

We claim:

1. A pharmaceutical formulation, being a unit dose sachet comprising granules of granular product containing amoxicillin trihydrate or ampicillin of 5% to 50% by weight and an effervescent couple which couple comprises a physiologically acceptable alkaline or alkaline earth metal carbonate as a basic ingredient and an acidic ingredient selected from the group consisting of citric acid, sodium hydrogen citrate, tartaric, adipic, fumaric and malic acid, the basic ingredient liberating carbon dioxide when it and the acidic ingredient are contacted with water, wherein the basic ingredient is present in 0.5% to 30% of the weight of the formulation and the acid ingredient is present in 0.5% to 20% of the weight of the formulation; and further wherein each granule contains both components of the effervescent couple and the amoxicillin trihydrate or ampicillin antibiotic.

2. A formulation according to claim 1 containing 40% to 50% by weight of the antibiotic.

3. A formulation according to claim 1 wherein the effervescent couple comprises citric acid or sodium hydrogen citrate and sodium bicarbonate.

4. A formulation according to claim 1 wherein the basic ingredient is selected from the group consisting of sodium bicarbonate, potassium bicarbonate, calcium bicarbonate and sodium glycine carbonate.

5. A formulation according to claim 1 wherein the acidic ingredient is present in the range 1% to 10% of the weight of the formulation.

6. A formulation according to claim 1 wherein the basic ingredient is present in the range 1.0% to 20% of the weight of the formulation.

7. A formulation according to claim 1 wherein the size of the granular product is in the range 30 to 600 μ.

8. A formulation according to claim 7 wherein the size of the granular product is in the range 100 to 425 μ.

9. A formulation according to claim 1 having a composition within ±10% of the following:

| Amoxycillin trihydrate equivalent to amoxycillin free acid | 41.667 wt % |
| --- | --- |
| Magnesium stearate | 1.125 wt % |
| Citric acid | 2.083 wt % |
| Sodium bicarbonate | 4.167 wt % |
| Sodium saccharin | 0.417 wt % |
| Lemon dry flavour | 4.583 wt % |
| Lime dry flavour | 0.230 wt % |
| Sorbitol BP | 15.000 wt % |
| Mannitol USP | 30.720 wt % |

10. A method of treatment of bacterial infections in human or animal patients which comprises the administration of a therapeutically effective amount of a pharmaceutical formulation according to claim 1.

11. A formulation according to claim 6 wherein the basic ingredient is present in the range of 1.5% to 10% of the weight of the formulation.

* * * * *